(12) United States Patent
Lerdworatawee et al.

(10) Patent No.: US 10,058,706 B2
(45) Date of Patent: Aug. 28, 2018

(54) BI-DIRECTIONAL SWITCHING REGULATOR FOR ELECTROCEUTICAL APPLICATIONS

(71) Applicant: QUALCOMM Incorporated, San Diego, CA (US)

(72) Inventors: Jongrit Lerdworatawee, Santee, CA (US); Chunlei Shi, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 13 days.

(21) Appl. No.: 15/261,695

(22) Filed: Sep. 9, 2016

(65) Prior Publication Data

US 2018/0071535 A1 Mar. 15, 2018

(51) Int. Cl.
| | |
|---|---|
| *A61N 1/00* | (2006.01) |
| *A61N 1/36* | (2006.01) |
| *A61N 1/05* | (2006.01) |
| *A61N 1/378* | (2006.01) |

(52) U.S. Cl.
CPC ....... *A61N 1/36125* (2013.01); *A61N 1/0551* (2013.01); *A61N 1/3605* (2013.01); *A61N 1/3787* (2013.01)

(58) Field of Classification Search
CPC .............. A61N 1/36125; A61N 1/0551; A61N 1/3787; A61N 1/3605
See application file for complete search history.

(56) References Cited

U.S. PATENT DOCUMENTS

| | | | |
|---|---|---|---|
| 5,423,866 A | 6/1995 | Ekwall | |
| 6,069,803 A | 5/2000 | Cross | |
| 6,871,090 B1 | 3/2005 | He et al. | |
| 6,909,915 B2 | 6/2005 | Greatbatch et al. | |
| 8,610,405 B2 | 12/2013 | Yamazaki et al. | |
| 2003/0132712 A1* | 7/2003 | Wood ..................... | H05B 33/08 315/169.3 |
| 2006/0271110 A1 | 11/2006 | Vernon et al. | |
| 2013/0035735 A1 | 2/2013 | Kroll | |
| 2013/0310894 A1 | 11/2013 | Trier | |

(Continued)

FOREIGN PATENT DOCUMENTS

| | | |
|---|---|---|
| CN | 103825329 A | 5/2014 |
| JP | 2005166829 A | 6/2005 |

OTHER PUBLICATIONS

Ji-Jon Sit, et al., A Low-Power Blocking-Capacitor-Free Charge-Balanced Electrode-Stimulator Chip With Less Than 6 nA DC Error for 1-mA Full-Scale Stimulation, IEEE Transactions on Biomedical Circuits and Systems, vol. 1, No. 3, Sep. 2007, pp. 172-183.

(Continued)

*Primary Examiner* — George Manuel
(74) *Attorney, Agent, or Firm* — Loza & Loza, LLP/Qualcomm (57) ABSTRACT

In certain aspects, a method for providing electrical stimulation includes transferring energy from a battery to an electrode to charge the electrode, and, after the electrode is charged, transferring energy from the electrode to the battery to discharge the battery. The energy transferred from the electrode to the battery may include a portion of the energy transferred from the battery to the electrode.

15 Claims, 10 Drawing Sheets

(56) References Cited

U.S. PATENT DOCUMENTS

2016/0056663 A1    2/2016  Deng
2016/0131709 A1*   5/2016  Yoo .................. G01R 31/31721
                                                             324/762.01

OTHER PUBLICATIONS

Hyung-Min Lee, et al., A Power-Efficient Switched-Capacitor Stimulating System for Electrical/Optical Deep-Brain Stimulation, 2014 IEEE International Solid-State Circuits Conference, ISSCC 2014, Digest of Technical Papers, Feb. 12, 2014, pp. 414-416.

Shawn K. Kelly, et al., A Power-Efficient Neural Tissue Simulator With Energy Recovery, IEEE Transactions on Biomedical Circuits and Systems, vol. 5, No. 1, Feb. 2011, pp. 20-29.

International Search Report and Written Opinion—PCT/US2017/046778—ISA/EPO—dated Oct. 23, 2017.

\* cited by examiner

BI-DIRECTIONAL SWITCHING REGULATOR FOR ELECTROCEUTICAL APPLICATIONS

BACKGROUND

Field

Aspects of the present disclosure relate generally to switching regulators, and more particularly, to bi-directional switching regulators for electroceutical applications.

Background

An electroceutical device may be implanted in a patient and provide electrical stimulation to nerves in the patient to treat a disease and/or disorder of the patient. In this regard, the device (also referred to as a neural implant or implant device) may include an electrode, which is charged to provide electrical stimulus to the nerves.

SUMMARY

The following presents a simplified summary of one or more embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later.

A first aspect relates a device. The device includes a battery, an electrode, and a switching regulator having a first terminal coupled to the battery, and a second terminal coupled to the electrode. The device also includes a controller configured to operate the switching regulator to charge and discharge the electrode, wherein, to charge the electrode, the controller operates the switching regulator to transfer energy from the battery to the electrode, and, to discharge the electrode, the controller operates the switching regulator to transfer energy from the electrode to the battery.

A second aspect relates to a method for providing electrical stimulation. The method includes transferring energy from a battery to an electrode to charge the electrode, and, after the electrode is charged, transferring energy from the electrode to the battery to discharge the electrode.

A third aspect relates to an apparatus for providing electrical stimulation. The apparatus includes means for transferring energy from a battery to an electrode to charge the electrode, and means for, after the electrode is charged, transferring energy from the electrode to the battery to discharge the electrode.

To the accomplishment of the foregoing and related ends, the one or more embodiments include the features hereinafter fully described and particularly pointed out in the claims. The following description and the annexed drawings set forth in detail certain illustrative aspects of the one or more embodiments. These aspects are indicative, however, of but a few of the various ways in which the principles of various embodiments may be employed and the described embodiments are intended to include all such aspects and their equivalents.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

An electroceutical device may be implanted in a patient and provide electrical stimulation to nerves in the patient to treat a disease and/or disorder of the patient. In this regard, the device (also referred to as a neural implant or implant device) may include an electrode, which is charged to provide electrical stimulus to the nerves.

Figure 1:
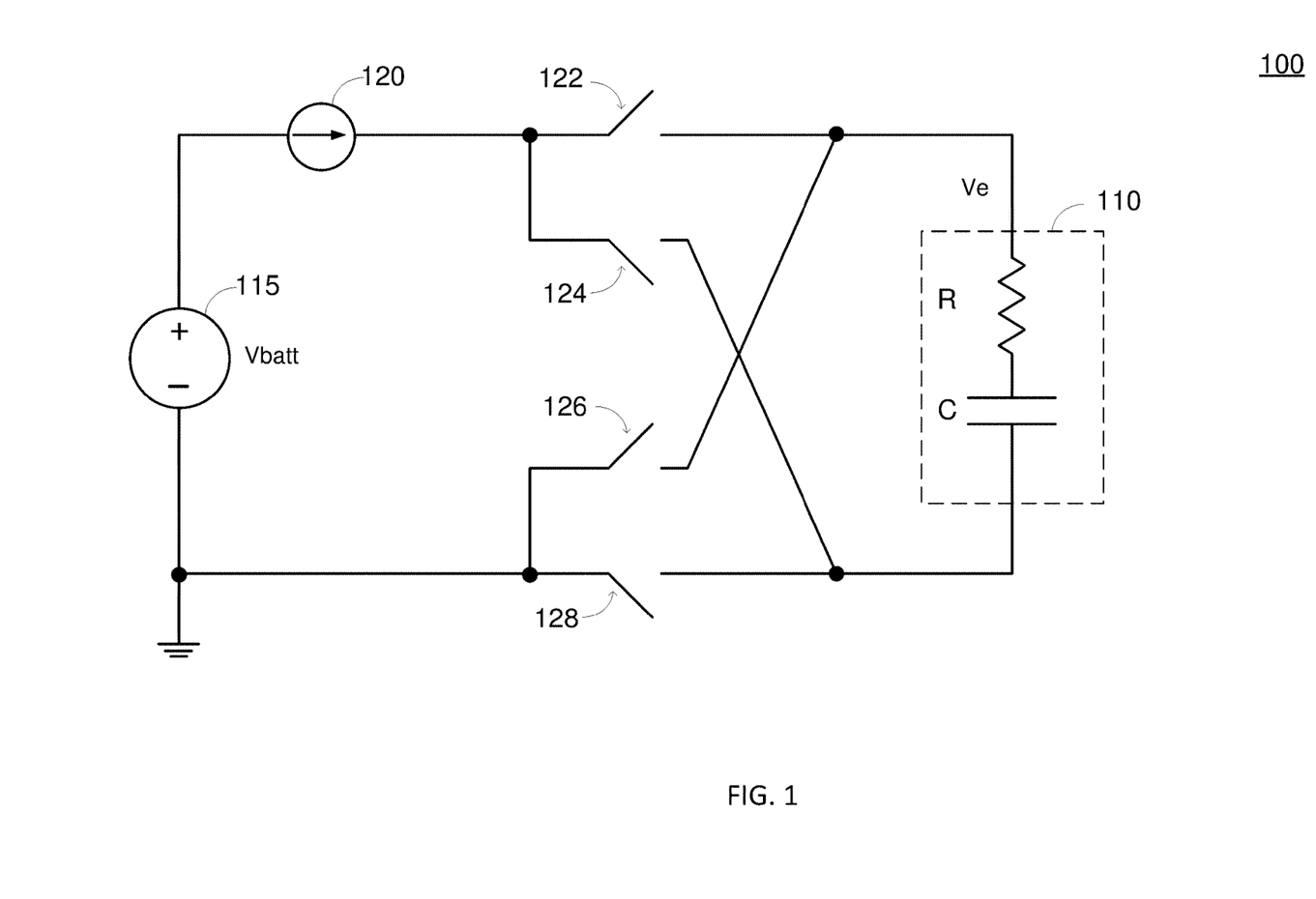
FIG. 1 shows an example of an electroceutical device.

FIG. 1 shows an example of an electroceutical device 100. The electroceutical device 100 includes an electrode 110, a battery 115, a current source 120, and switches 122, 124, 126 and 128. The electrode 110 may be electrically modeled as an RC circuit including a resistor R and a capacitor C in series, as shown in FIG. 1. The battery 110 provides an approximately fixed voltage Vbatt for the device 110, and the current source 120 is configured to regulate current flow to the electrode 110 to provide an approximately constant current to the electrode 110.

To provide electrical stimulation to nerves, the electrode 110 is charged and discharged. Since the electrode 110 is modeled as an RC circuit, the electrical stimulation can be viewed as a process of charging and discharging the RC circuit. To charge the electrode 110, switches 122 and 128 are closed (turned on) and switches 124 and 126 are opened (turned off). This allows the battery 115 to charge the electrode 110, in which the current source 120 regulates the current flow to the electrode 110 so that the current to the electrode 110 is approximately constant. To discharge the electrode 110, switches 124 and 126 are closed (turned on) and switches 122 and 128 are opened (turned off). This reverses the direction of the current at the electrode 110, causing the electrode 110 to discharge.

The electroceutical device 100 shown in FIG. 1 has several drawbacks that negatively impact the energy efficiency of the device 100. One drawback is that there is a large overhead voltage across the current source 120, resulting in a large amount of wasted energy. This is because the voltage Vbatt of the battery 115 is fixed and needs to be large in order to accommodate the full voltage range of the electrode 110. As a result, when the voltage Ve of the electrode 110 is small (e.g., at the start of charging), a large overhead voltage appears across the current source 120, resulting in a large amount of wasted energy. A second drawback is that the energy stored in the capacitor C of the electrode 110 after charging is dumped to ground during discharging instead of being recycled back to the battery 115. As a result, the energy stored in the capacitor C is wasted.

Accordingly, there is a need to address one or more of the drawbacks discussed above to improve energy efficiency, and therefore extend the battery life of an electroceutical device.

Figure 2:
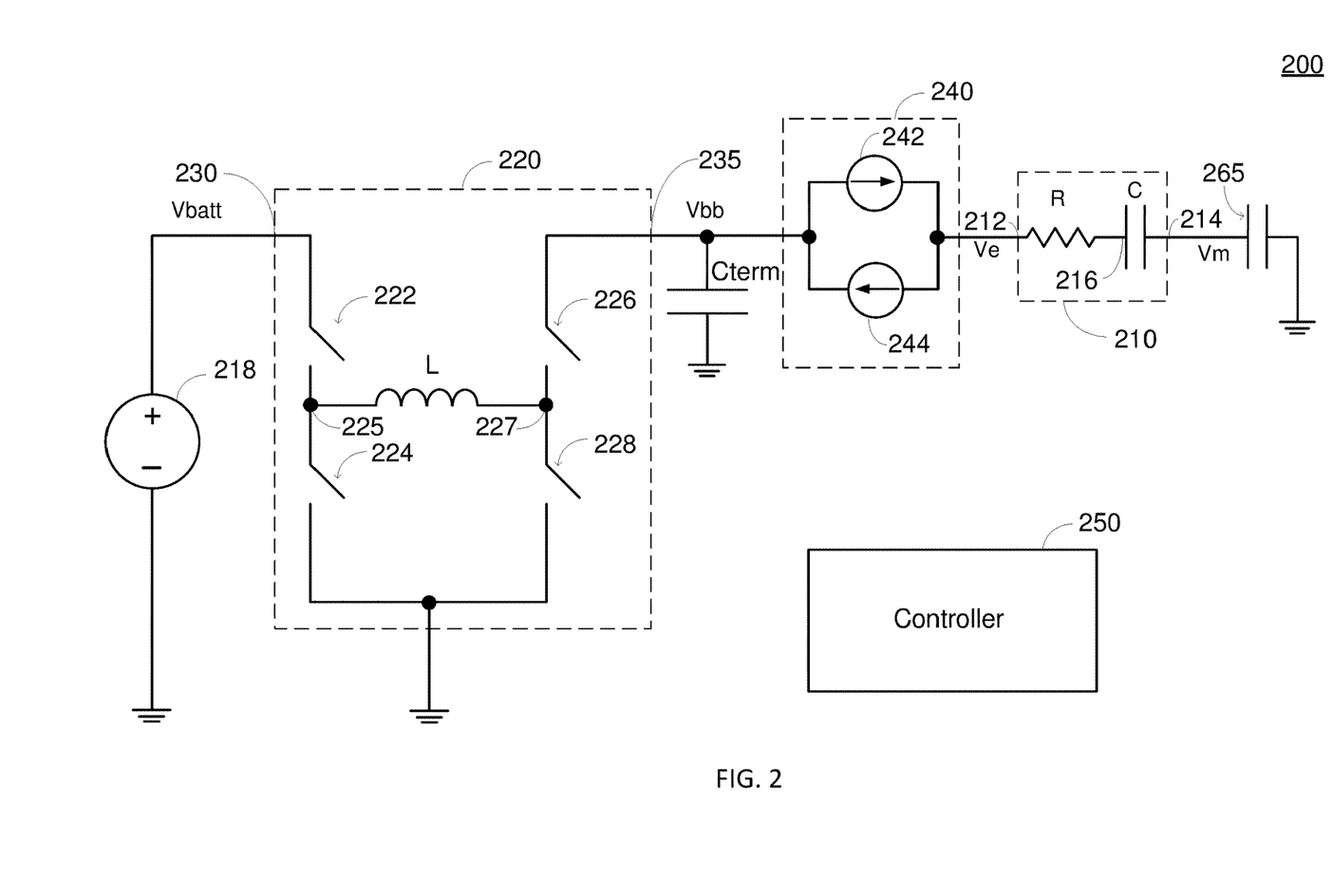
FIG. 2 shows an exemplary electroceutical device including a bi-directional switching regulator according to certain aspects of the present disclosure.

FIG. 2 below shows an electroceutical device 200 according to certain aspects of the present disclosure. The electroceutical device 200 includes an electrode 210, a battery 218, a bi-directional switching regulator 220, a bi-directional current source 240, a terminal capacitor Cterm, and a controller 250. The switching regulator 220 has a first terminal 230 coupled to the battery 218, and a second terminal 235 coupled to the bi-directional current source 240. The bi-directional current source 240 is coupled between the second terminal 235 of the switching regulator 220 and the electrode 210. The terminal capacitor Cterm is coupled between the second terminal 235 of the switching regulator 220 and ground.

In the example in FIG. 2, the electrode 210 is electrically modeled as an RC circuit including a resistor R and a capacitor C in series, in which the resistor R models the resistance of the electrode 210 and the capacitor C models the capacitance of the electrode 210. The electrode 210 has a first terminal 212 coupled to the bi-directional current source 240, and a second terminal 214 coupled to capacitor 265. The capacitor 265 is pre-charged to a voltage of Vm. Thus, the voltage at the second terminal 214 of the electrode 210 is set to Vm. As discussed further below, this allows the electrode 210 to be discharged without requiring a negative voltage.

In the example shown in FIG. 2, the switching regulator 220 is implemented with a bi-directional buck-boost converter to cover a wide input/output voltage range. The buck-boost converter is bi-directional in that the buck-boost converter is capable of transferring energy in either direction (i.e., from the first terminal 230 to the second terminal 235, or from the second terminal 235 to the first terminal 230). For a given input voltage, the buck-boost converter is capable of boosting the input voltage to produce an output voltage that is greater than the input voltage, or bucking the input voltage to produce an output voltage that is less than the input voltage, as discussed further below. Thus, the output voltage range of the buck-boost converter covers output voltages greater than the input voltage and output voltages less than the input voltage.

In the example in FIG. 2, the switching regulator 220 includes an inductor L, a first switch 222, a second switch 224, a third switch 226, and a fourth switch 228. The first switch 222 is coupled between the first terminal 230 of the switching regulator 220 and a first terminal 225 of the inductor L. The second switch 224 is coupled between the first terminal 225 of the inductor L and ground. The third switch 226 is coupled between the second terminal 235 of the switching regulator 220 and a second terminal 227 of the inductor L. Finally, the fourth switch 228 is coupled between the second terminal 227 of the inductor L and ground. The controller 250 controls operation of the switching regulator 220 by controlling the on/off states of the switches 222, 224, 226 and 228, as discussed further below. For ease of illustration, the individual connections between the controller 250 and the switches 222, 224, 226 and 228 are not shown in FIG. 2. The switches 222, 224, 226 and 228 may be implemented with n-type field effect transistor (NFET) switches, p-type field effect transistor (PFET) switches, or a combination thereof.

The bi-directional current source 240 is configured to provide an approximately constant current in either direction under the control of the controller 250. In this regard, the bi-directional current source 240 includes a first current source 242 configured to provide an approximately constant current for charging the electrode 210, and a second current source 244 configured to provide an approximately constant current for discharging the electrode 210. Each of the current sources may be implemented with a current mirror or another type of circuit. In operation, the controller 250 activates one of the current sources 242 and 244 one at a time, as discussed further below. For ease of illustration, the individual connections between the controller 250 and the current sources 242 and 244 are not shown in FIG. 2.

The electroceutical device 200 provides electrical stimulation to nerves by charging and discharging the electrode 210. In this regard, the charging operation is discussed in detail below according to certain aspects followed by the discharging operation.

To charge the electrode 210, the controller 250 activates the first current source 242 and deactivates the second current source 244 so that the direction of current flow is toward the electrode 210. The controller 250 then switches the switches 222, 224, 226 and 228 on/off over multiple switching cycles. Each switching cycle includes a first phase $\phi$ and a second phase $\bar{\phi}$.

During the first phase $\phi$ of each cycle, the controller 250 closes (turns on) switches 222 and 228, and opens (turns off) switches 224 and 226. As a result, the first terminal 225 of the inductor L is coupled to the battery 218 and the second terminal 227 of the inductor L is coupled to ground. This allows the battery 218 to energize the inductor L.

During the second phase $\bar{\phi}$ of each cycle, the controller 250 closes (turns on) switches 224 and 226, and opens (turns off) switches 222 and 228. As a result, the first terminal 225 of the inductor L is coupled to ground and the second terminal 227 of the inductor L is coupled to the terminal capacitor Cterm. This causes the switching regulator 220 to dump the energy in the inductor L to the terminal capacitor Cterm. The energy then flows form the terminal capacitor Cterm to the electrode 210 through the first current source 242. Thus, during charging, the switching regulator 220 transfers energy from the first terminal 230 to the second terminal 235. The terminal capacitor Cterm helps hold the voltage Vbb at the second terminal 235 of the switching regulator 220 during the first phase $\phi$ of each switching cycle when the inductor L is decoupled from the second terminal 235.

The first current source 242 regulates the current flow to the electrode 210 such that an approximately constant current flows to the electrode 210. The approximately constant current allows the capacitor C of the electrode 210 to be precisely charged by controlling the duration of the charging, as discussed further below.

The switching regulator 220 may charge the capacitor C of the electrode 210 over many switching cycles (e.g., 100s or 1000s of cycles). As discussed further below, the controller 250 may adjust the voltage Vbb at the second terminal 235 of the switching regulator 220 during charging of the electrode 210 by dynamically adjusting the durations of the first and second phases $\phi$ and $\bar{\phi}$ of the switching cycles during charging of the electrode 210. For example, the switching regulator 220 may have a duty cycle, which may be defined as the duration of the first phase $\phi$ over the sum of the durations of the phases $\phi$ and $\bar{\phi}$. In this example, the controller 250 may increase voltage Vbb by increasing the duty cycle of the switching regulator 220, and decrease voltage Vbb by decreasing the duty cycle of the switching regulator 220. In the example shown in FIG. 2 in which the switching regulator 220 is implemented with a buck-boost converter, the switching regulator 220 is capable of adjusting voltage Vbb to voltage levels above and below the input voltage. For instance, the switching regulator 220 may boost the input voltage for a duty cycle greater than 50%, and buck the input voltage for a duty cycle less than 50%.

Figure 3A:
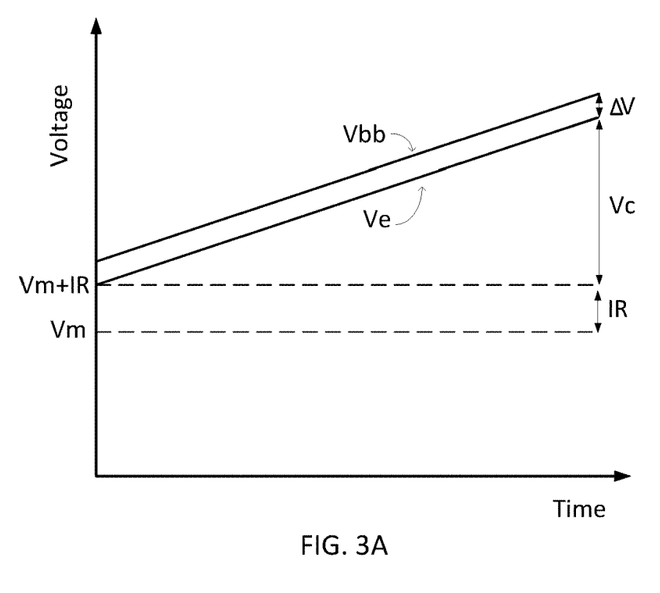
FIG. 3A shows an exemplary output voltage of the switching regulator during charging of an electrode according to certain aspects of the present disclosure.

Since the current flow into the electrode 210 is approximately constant due to the first current source 242, the voltage across the capacitor C of the linearly increases (ramps up) during charging. An example of this is shown in FIG. 3A, which shows the voltage Ve at terminal 212 of the electrode 210 during charging. At the start of charging, the voltage Ve is approximately equal to Vm plus the IR voltage drop across the resistor R of the electrode 210. The IR voltage drop remains approximately constant during charging because of the approximately constant current (denoted "I" in FIG. 3A) provided by the first current source 242. As the capacitor C charges up, the voltage across the capacitor (denoted "Vc" in FIG. 3A) linearly increases (ramps up). This causes the voltage Ve at terminal 212 of the electrode to also linearly increase (ramp up), as shown in FIG. 3A.

During charging, the controller 250 may dynamically adjust the voltage Vbb at the second terminal 235 of the switching regulator 220 (e.g., by adjusting the duty cycle of the switching regulator 220) to keep the overhead voltage across the first current source 242 low (e.g., close to the minimum overhead voltage needed for the first current source 242 to operate properly). This substantially reduces the amount of wasted energy compared to the device 100 in FIG. 1, as discussed further below.

FIG. 3A shows an example in which the controller 250 adjusts the voltage Vbb to track the increase in the voltage Ve of the electrode 210 during charging. For example, the controller 250 may increase (e.g., ramp up) Vbb at approximately the same rate as Ve to keep Vbb above Ve by a small voltage margin $\Delta V$, as shown in FIG. 3A. The voltage margin $\Delta V$ may be set to a voltage that provides just enough overhead voltage across the first current source 242 for the first current source 242 to operate properly. By keeping the overhead voltage across the first current source 242 low, the amount of wasted energy due to the overhead voltage is substantially reduced compared to the device 100 in FIG. 1, in which the battery 115 is coupled directly to the electrode 110 without a switching regulator.

Figure 3B:
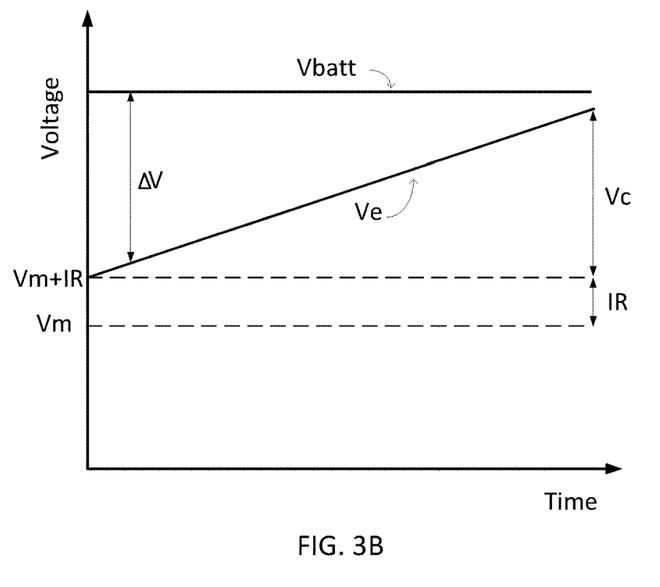
FIG. 3B shows an example of a fixed battery voltage during charging of an electrode.

This can be explained with reference to FIG. 3B, which shows the voltage Vbatt of the battery 218 for the case in which the battery 218 is coupled directly to the first current source 242 without the switching regulator 220. In this case, the voltage Vbatt of the battery 218 needs to be above the maximum voltage of the electrode 210 in order to accommodate the voltage range of the electrode 210. As shown in FIG. 3B, the voltage margin $\Delta V$ is large at the start of charging, resulting in a large overhead voltage across the first current source 242. The large overhead voltage leads to a much larger amount of wasted energy compared with FIG. 3A.

Unlike the electroceutical device 100 in FIG. 1, the electroceutical device 200 in FIG. 2 does not require that the battery voltage Vbatt be above the maximum voltage of the electrode 210. This is because the switching regulator 220 (which is implemented with a buck-boost converter in FIG. 2) is capable of boosting the battery voltage Vbatt if needed to charge the electrode 210.

To discharge the electrode 210, the controller 250 activates the second current source 244 and deactivates the first current source 242 so that the direction of current flow is away from the electrode 210. The second current source 244 regulates the discharging current so that the discharging current is approximately constant. This allows the capacitor C to be precisely discharged by controlling the duration of the discharging, as discussed further below.

The controller 250 then switches the switches 222, 224, 226 and 228 on/off over multiple switching cycles. Each switching cycle includes a first phase $\phi$ and a second phase $\bar{\phi}$. During the first phase $\phi$ of each cycle, the controller 250 closes (turns on) switches 224 and 226, and opens (turns off) switches 222 and 228. As a result, the first terminal 225 of the inductor L is coupled to ground and the second terminal 227 of the inductor L is coupled to the terminal capacitor Cterm. This causes energy to transfer from the electrode 210 to the inductor L. During the second phase $\bar{\phi}$ of each cycle, the controller 250 closes (turns on) switches 222 and 228, and opens (turns off) switches 224 and 226. As a result, the first terminal 225 of the inductor L is coupled to the battery 218 and the second terminal 227 of the inductor L is coupled to ground. This causes the switching regulator 220 to dump the energy in the inductor L to the battery 218. Thus, a portion of the energy stored in the capacitor C of the electrode 210 is recycled back to the battery 218 thereby improving energy efficiency. Note that some of energy stored in the capacitor C is lost through the resistor R.

The switching regulator 220 may discharge the capacitor C of the electrode 210 over many switching cycles (e.g., 100s or 1000s of cycles). Thus, during discharging, the switching regulator 220 transfers energy from the second terminal 235 to the first terminal 230 (i.e., reverses the direction of energy flow relative to the direction of energy flow for charging).

Since the current flow out of the electrode 210 is approximately constant due to the second current source 244, the voltage across the capacitor C of the linearly decreases during discharging. During discharging, the controller 250 may adjust voltage Vbb (e.g., by adjusting the duty cycle of the switching regulator 220) so that voltage Vbb stays below the voltage Ve by the voltage margin $\Delta V$. Note that Vbb is below Ve for discharging because the direction of current flow is reversed relative to charging. The voltage margin $\Delta V$ may to be set to a voltage that provides just enough overhead voltage for the second current source 244 to operate properly.

In certain aspects, the controller 250 may discharge the electrode 215 until the voltage across the capacitor C is approximately zero (i.e., until the voltage at terminal 216 of the capacitor C is approximately equal to the voltage Vm at terminal 214 of the capacitor C). This may be done so that the electrical stimulation operation results in approximately no net accumulation of charge on the capacitor C. To discharge the capacitor C until terminal 216 reaches the voltage Vm, the controller 250 may decrease the voltage Vbb at the second terminal 235 of the switching regulator 220 until Vbb reaches a voltage approximately equal to Vm−(IR+ΔV), where IR is the voltage drop across the resistor R. The voltage Vm at terminal 214 of the capacitor C allows the switching regulator 220 to discharge the capacitor C without requiring the voltage Vbb to be negative. In contrast, if terminal 214 of the capacitor C were coupled to ground, then the voltage Vbb would need to go negative in order to discharge the capacitor C.

Figure 4:
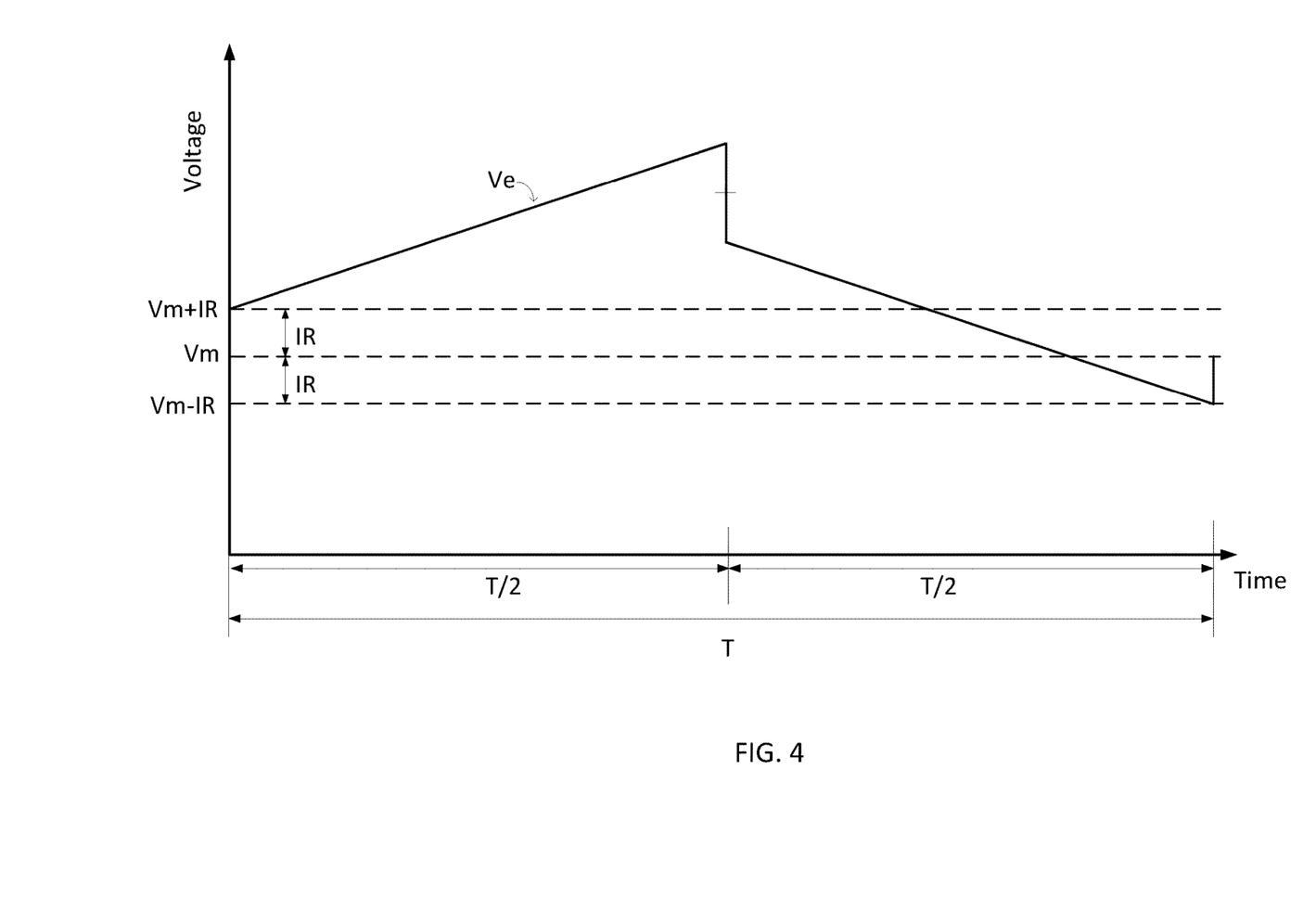
FIG. 4 shows a voltage of an electrode during an electrical stimulation operation according to certain aspects of the present disclosure.

FIG. 4 shows an example of the voltage Ve of the electrode 210 during a stimulation operation. During charging, the voltage Ve of the electrode 210 may be approximately equal to Vm+(Vc+IR), where IR is the voltage drop across the resistor and Vc is the voltage across the capacitor C. IR is approximately constant due the constant charging current provided by the first current source 242, and Vc linearly increases (ramps up), as shown in FIG. 4. During charging, the controller 250 may adjust Vbb (not shown in FIG. 4) to keep Vbb just high enough above Ve to provide enough overhead voltage for the first current source 242 to operate properly, as discussed above. For example, the controller 250 may ramp up Vbb at approximately the same rate as Ve to keep Vbb above Ve by the voltage margin.

During discharging, the voltage Ve of the electrode 210 may be approximately equal to Vm+(Vc−IR). As shown in FIG. 4, the voltage across the capacitor C linearly decreases (ramps down) due to the approximately constant discharging current provided by the second current source 244. In addition, the IR voltage drop across the resistor changes polarity since the direction of current flow is reversed for discharging. During discharging, the controller 250 may adjust Vbb (not shown in FIG. 4) to keep Vbb just low enough below Ve to provide enough overhead voltage for the second current source 244 to operate properly, as discussed above.

As discussed above, the charging and discharging of the electrode 210 may be balanced so that the electrical stimulation operation results in approximately no net accumulation of charge on the capacitor C. If the first and second current sources 242 and 244 are configured to provide approximately the same constant current, this may be accomplished by making the duration of the charging approximately equal to the duration of the discharging. For instance, if the duration of the electrical stimulation operation is denoted "T", then the duration of the charging is approximately T/2 and the duration of the discharging is approximately T/2, an example of which is shown in FIG. 4.

As discussed above, the switching regulator 220 may charge and discharge the electrode 210 over many switching cycles (e.g., 100s or 1000s of cycles). For example, the controller 250 may switch the switches 222, 224, 226 and 228 at a frequency in the MHz range, in which case each switching cycle may be on the order of a few microseconds or less. In this example, the duration of the electrical stimulation operation T may be on the order of 100s of microseconds or milliseconds.

Thus, in certain embodiments, the controller 250 may adjust the voltage Vbb at the second terminal 235 of the switching regulator 220 to keep Vbb just high enough above the voltage Ve of the electrode 210 for the first current source 242 to operate properly. This substantially reduces the overhead voltage across the current source during charging, thereby improving energy efficiency.

In certain embodiments, the controller 250 may operate the voltage controller 250 to transfer a portion of the energy stored in the electrode 210 back to the battery 218 during discharging of the electrode 210. Thus, a portion of the energy stored in the electrode 210 is recycled back the battery 218, thereby improving energy efficiency. In contrast, in the device 100 in FIG. 1, all of the energy stored in the electrode 110 is dumped to ground, and is therefore wasted.

Figure 5:
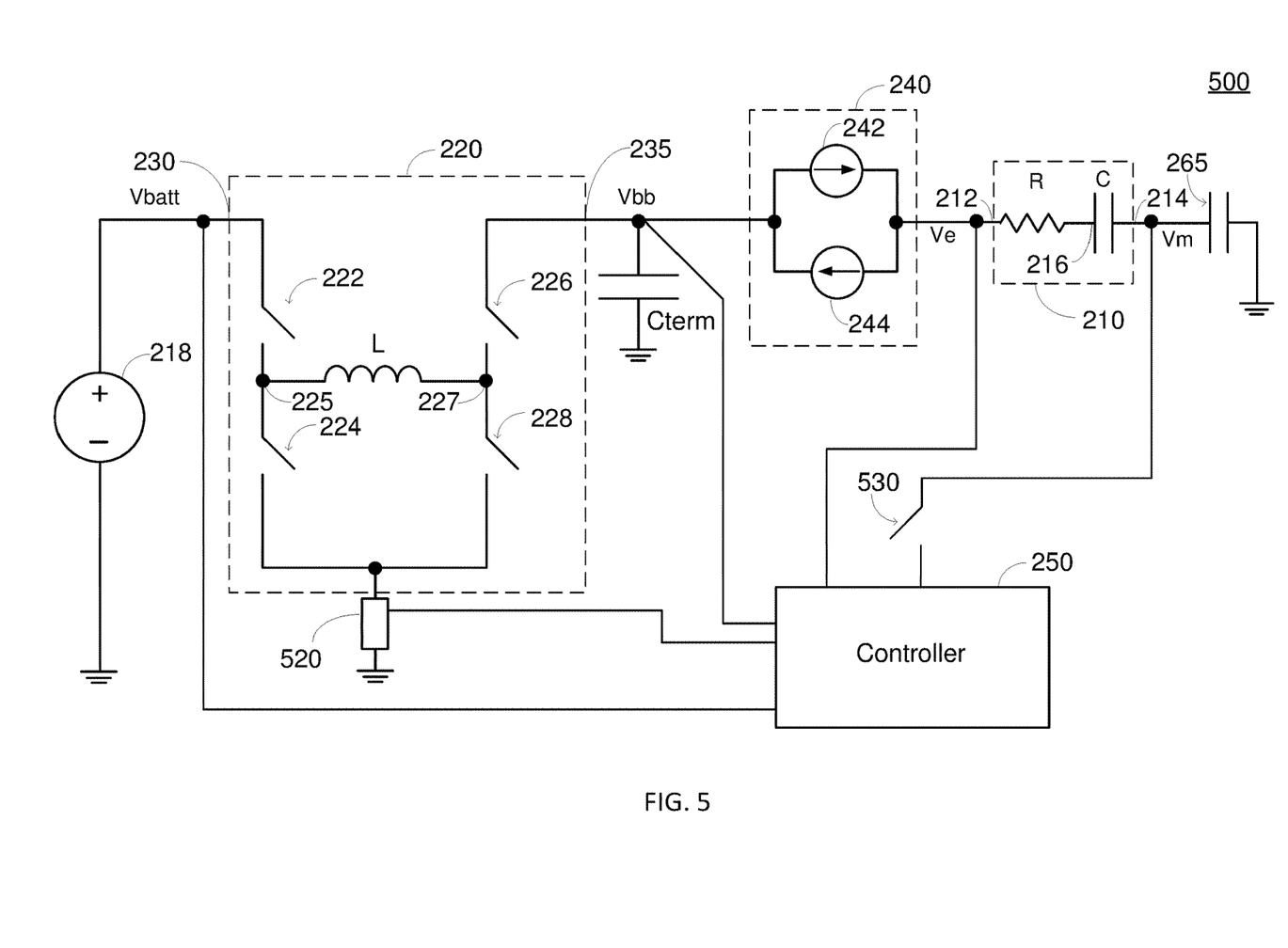
FIG. 5 shows another example of an electroceutical device including a bi-directional switching regulator according to certain aspects of the present disclosure.

In certain aspects, the controller 250 may sense the voltage Vbb at the second terminal 235, and adjust the voltage Vbb based on the sensed voltage. In this regard, FIG. 5 shows an example in which the second terminal 235 is coupled to the controller 250 to allow the controller 250 to sense voltage Vbb. In this example, the controller 250 may determine a target voltage for the voltage Vbb during charging of the electrode 210. For example, the target voltage may be approximately equal to the voltage Ve of the electrode 210 plus the voltage margin ΔV discussed above. The controller 250 may then compare the sensed voltage Vbb with the target voltage for Vbb and adjust voltage Vbb (e.g., by adjusting the duty cycle of the switching regulator 220) in a direction that reduces the difference (error) between the sensed voltage Vbb and the target voltage. Thus, in this example, the controller 250 adjusts the voltage Vbb at the second terminal of the switching regulator 220 based on feedback of the voltage Vbb.

As discussed above, the target voltage may be approximately equal to the voltage Ve of the electrode 210 plus the voltage margin ΔV. The controller 250 may determine voltage Ve by sensing voltage Ve during charging. In this regard, FIG. 5 shows an example in which the controller 250 is coupled to terminal 212 of the electrode 210 to allow the controller 250 to sense voltage Ve. In this example, the controller 250 may determine the target voltage for Vbb by adding the voltage margin ΔV to the sensed voltage Ve. The voltage margin ΔV may be close to the minimum overhead voltage needed for the current source 240 to properly operate.

Alternatively, the controller 250 may compute voltage Ve. Assuming that the current of the first current source 242 is known and the capacitance of capacitor C is known, the controller 250 may use this information to compute Ve during charging. In this example, the controller 250 may determine the target voltage for Vbb by adding the voltage margin ΔV to the computed voltage Ve.

The controller 250 also use the feedback mechanism discussed above to adjust the voltage Vbb at the second terminal 235 of the switching regulator 220 during discharging. In this case, the target voltage may be approximately equal to the voltage Ve of the electrode 210 minus the voltage margin ΔV.

In certain aspects, the controller 250 may use hysteretic feedback control to adjust voltage Vbb. In these aspects, the controller 250 may also be configured to sense the current of the inductor L. To do this, the electroceutical device 500 may also include a current sensor 520 coupled between switches 224 and 228 and ground, as shown in FIG. 5. The current sensor 520 may be implemented, for example, with a low-resistance sense resistor. In this example, the controller 250 may sense the current passing through the sense resistor (and hence the inductor L) by sensing the IR voltage drop across the sense resistor. It is to be appreciated that the current sensor 520 is not limited to the location shown in FIG. 5, and may be placed at another location on the device 500 to sense the inductor current. Also, it is to be appreciated that the device 500 may employ more than one current sensor to sense the inductor current.

An example of hysteretic feedback control during charging of the electrode 210 will now be discussed with reference to the timing diagram 600 in FIG. 6. The timing diagram 600 shows an example of the voltage Vbb at the second terminal 235 of the switching regulator 220, an example of the inductor current (denoted "IL" in FIG. 6), an example of durations of phase ϕ (denoted "phi" in FIG. 6), and an example of durations of phase $\bar{\phi}$ (denoted "phib" in FIG. 6). An example of the target voltage (denoted "Vtarget") is also shown.

In this example, the controller 250 turns on the switching regulator 220 when the sensed voltage Vbb falls below the target voltage. This is indicated by the "on" signal in FIG. 6, which transitions from low to high when Vbb falls below the target voltage. This is done to conserve power by reducing switching activity of the switching regulator 220.

When the switching regulator 220 is turned on, the controller 250 initiates a switching cycle of the switching regulator 220, in which the switching cycle includes a first phase ϕ and a second phase $\bar{\phi}$. In the first phase ϕ of the cycle, the controller 250 turns on switches 222 and 228 and turn off switches 224 and 226 to energize the inductor L until the sensed inductor current reaches a current limit (denoted "ilimit" in FIG. 6). Thus, the first phase ϕ ends when the sensed inductor current reaches the current limit. The controller 250 then starts the second phase $\bar{\phi}$ of the cycle. In the second phase $\bar{\phi}$, the controller turns on switches 224 and 226 and turns off switches 222 and 228 to transfer the energy in the inductor L to the electrode 210. The duration of the second phase $\bar{\phi}$ is a minimum of a fixed time limit (denoted "Toff" in FIG. 6) and a zero-crossing time (denoted "izero" in FIG. 6), in which the zero-cross time occurs when the sensed inductor current is approximately zero.

At the end of the cycle, the controller 250 determines whether voltage Vbb is still below the target voltage. If voltage Vbb is above the target voltage, then the controller 250 may turn off the switching regulator 220 until the sensed voltage Vbb falls below the target voltage again. If voltage Vbb is still below the target voltage, then the controller 250 may initiate another switching cycle of the switching regulator 220, as discussed above. The controller 250 may continue to initiate switching cycles until the sensed voltage Vbb rises above the target voltage.

Thus, when the sensed voltage Vbb falls below the target voltage, the controller 250 turns on the switching regulator 220, and operates the switching regulator 220 to transfer energy from the first terminal 230 to the second terminal 235 over one or more switching cycles until the sensed voltage Vbb rises above the target voltage. Although the target voltage is shown being fixed in FIG. 6 for simplicity, it is to be appreciated that the target voltage may change over time. For example, the target voltage may track changes in the voltage Ve of the electrode 210 to keep the target voltage above the voltage Ve by the voltage margin ΔV, as discussed above.

Figure 6:
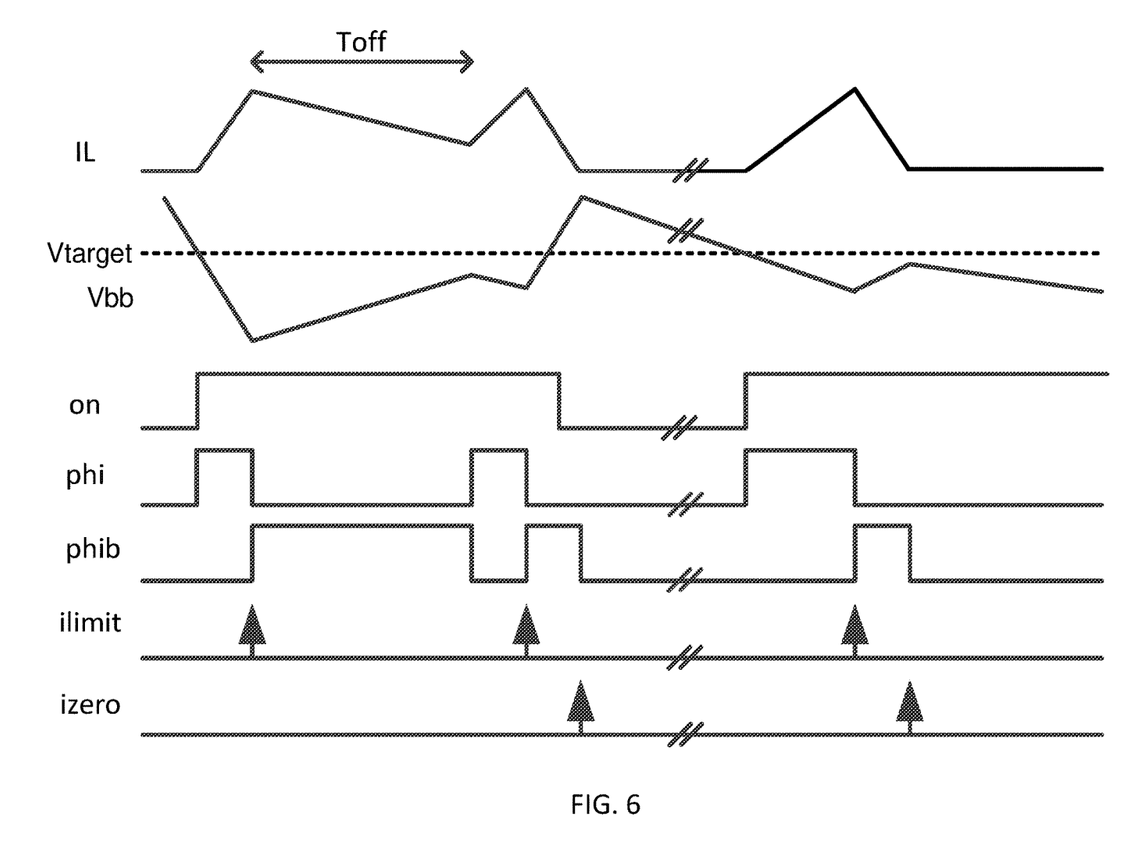
FIG. 6 is a timing diagram illustrating an example of hysteretic feedback control according to certain aspects of the present disclosure.

As shown in FIG. 6, voltage Vbb may fluctuate about the target voltage by a small amount. In this regard, the voltage margin ΔV may be set to a voltage slightly above the minimum overhead voltage needed for the current source 240 to operate to provide enough headroom to accommodate fluctuations of Vbb about the target voltage. For example, the voltage margin ΔV may be set to a voltage equal to or less than twice the minimum overhead voltage for the current source to operate. In another example, the voltage margin ΔV may be set to a voltage equal to or less than 150% of the minimum overhead voltage for the current source to operate. In one aspect, the minimum overhead voltage may correspond to a voltage across the current source at which the current deviates from the constant current by 10%.

The exemplary hysteretic feedback control discussed above may also be used to adjust the voltage Vbb during discharging of the electrode 210. In this case, the controller 250 reverses the switching sequence of the switches so that the inductor L is coupled to the second terminal 235 during the first phase ϕ (denoted "phi" in FIG. 6) and the inductor L is coupled to the first terminal 230 during second phase $\bar{\phi}$ (denoted "phib" in FIG. 6). This is done to reverse the flow of energy from the electrode 210 to the battery 218, as discussed above.

It is to be appreciated that the hysteretic feedback control illustrated in FIG. 6 is exemplary only, and that the controller 250 may employ another feedback control mechanism.

In certain aspects, the controller 250 may pre-charge capacitor 265 to set the voltage Vm at terminal 214 of the capacitor C. In this regard, the electroceutical device 500 may further include a switch 530 coupled between capacitor 265 and the controller 250, as shown in FIG. 5. To pre-charge capacitor 265, the controller 250 may close (turn on) switch 530 to couple the controller 250 to capacitor 265. The controller 250 may then pre-charge capacitor 265 to the voltage Vm, in which the voltage Vm may be a voltage that is high enough to allow the switching regulator 220 to discharge the capacitor C without requiring a negative voltage. After capacitor 265 is pre-charged to Vm, the controller 250 may open switch 530.

An electroceutical device may employ energy harvesting to power the device. For example, the device may include a wireless charging coil configured to receive energy wirelessly from an external power source via a wireless signal (e.g., RF signal). This allows energy to be transferred from the external power source to the device through the patient. The electroceutical may store the received energy in the battery of the device for later use (e.g., provide electrical stimulation to the patient).

Figure 7:
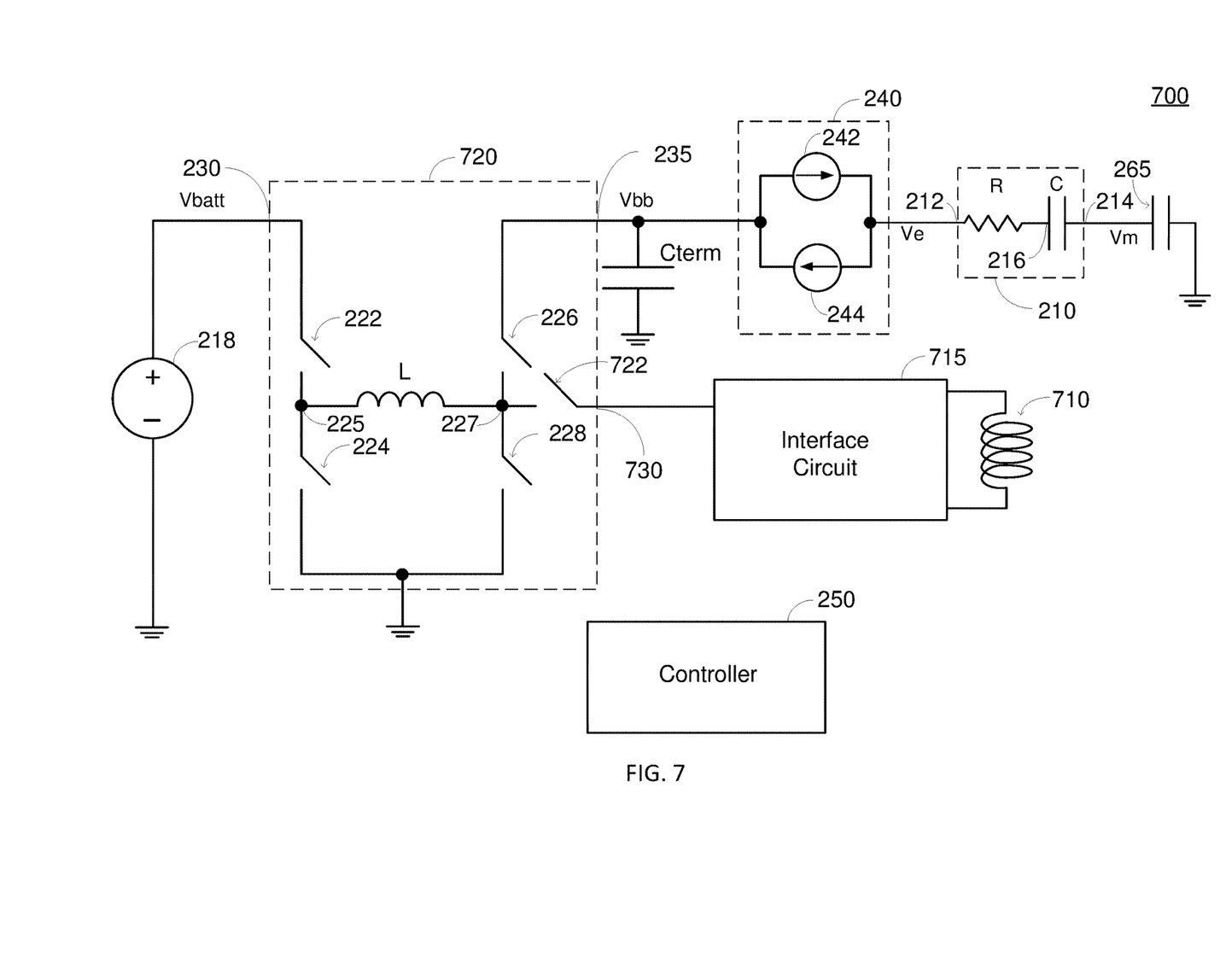
FIG. 7 shows an example of an electroceutical device including a wireless charging coil according to certain aspects of the present disclosure.

In this regard, FIG. 7 shows an example in which the electroceutical device 700 also includes a wireless charging coil 710 according to certain aspects. The wireless charging coil 710 is configured to receive energy wirelessly from an external power source (not shown) via a wireless signal. The device 700 further includes an interface circuit 715 configured to interface the wireless charging coil 710 with the switching regulator 720, as discussed further below.

In this example, the switching regulator 720 includes the inductor L and switches 222, 224, 226 and 228 discussed above. The switching regulator 720 further includes a fifth switch 722 coupled between the second terminal 228 of the inductor L and a third terminal 730 of the switching regulator 720. The interface circuit 715 is coupled between the third terminal 730 of the switching regulator 720 and the wireless charging coil 710. In operation, the wireless charging coil 710 receives a wireless signal from the external power source, and converts the received signal into an AC signal. The interface circuit 715 is configured to rectify the AC signal from the wireless charging coil 710 into a DC voltage, and output the DC voltage to the third terminal 730 of the switching regulator 220.

In certain aspects, the controller 250 time-multiplexes the switching regulator 720 between charging the battery 218 using the wireless charging coil 710 and providing electrical stimulation via the electrode 210. To provide electrical stimulation, the controller 250 opens (turns off) switch 722 to decouple (electrically isolate) the inductor L from the wireless charging coil 710. The controller 250 then charges and discharges the electrode 210 as discussed above. The controller 250 may perform one or more electrical stimulation operations while switch 722 is opened. Switch 722 remains open while electrical stimulation operations are being performed.

To charge the battery 218 using energy harvested by the wireless charging coil 710, the controller opens (turns off) switch 226 to decouple (electrically isolate) the inductor L from the electrode 210. The controller 250 then switches the switches 222, 224, 228 and 730 on/off over one or more switching cycles to transfer energy from the wireless charging coil 710 to the battery 218. Each switching cycle includes a first phase $\phi$ and a second phase $\bar{\phi}$. During the first phase $\phi$ of each cycle, the controller 250 closes (turns on) switches 722 and 224, and opens (turns off) switches 222 and 228. As a result, the second terminal 227 of the inductor L is coupled to the wireless charging coil 710 via the interface circuit 715, and the first terminal 225 of the inductor L is coupled to ground. This allows the wireless charging coil 710 to energize the inductor L with energy received from the wireless signal from the external power source. During the second phase $\bar{\phi}$ of each cycle, the controller 250 opens (turns off) switches 722 and 224, and closes (turns on) switches 222 and 228. As a result, the first terminal 225 of the inductor L is coupled to the battery 218, and the second terminal 227 of the inductor is coupled to ground. This transfers the energy stored in the inductor L to the battery 218, thereby charging the battery 218. Switch 226 remains open while the battery 218 is being charged by the wireless charging coil 710.

During charging of the battery 218 by the wireless charging coil 710, the controller 250 may adjust the duty cycle of the switching regulator 720 to convert the DC voltage at the third terminal 730 to a voltage approximately equal to the battery voltage Vbatt at the first terminal 230. In the example in FIG. 7 in which the switching regulator 720 is implemented with a buck-boost converter, the DC voltage can be either greater than or less than the battery voltage Vbatt. This is because the switching regulator 720 can either boost or buck the DC voltage (e.g., depending on the duty cycle of the switching regulator 220).

Thus, the switching regulator 720 may be time-multiplexed between charging the battery 218 using the wireless charging coil 710 and providing electrical stimulation to the patient. This allows the inductor L of the switching regulator 720 to be shared by the battery charging operation and electrical stimulation operation of the device 700, thereby reducing the size of the device 700.

In the battery charging operation, the switching regulator 720 transfers energy from the wireless charging coil 710 to the battery 218 through the inductor L to charge the battery 218. In the electrical stimulation operation, energy is transferred in both directions. More particularly, the switching regulator 720 transfers energy from the battery 218 to the electrode 210 through the inductor L to charge the electrode 210. The switching regulator 720 then transfers energy from the electrode 210 to the battery 218 through the inductor L to discharge the electrode 210.

Figure 8:
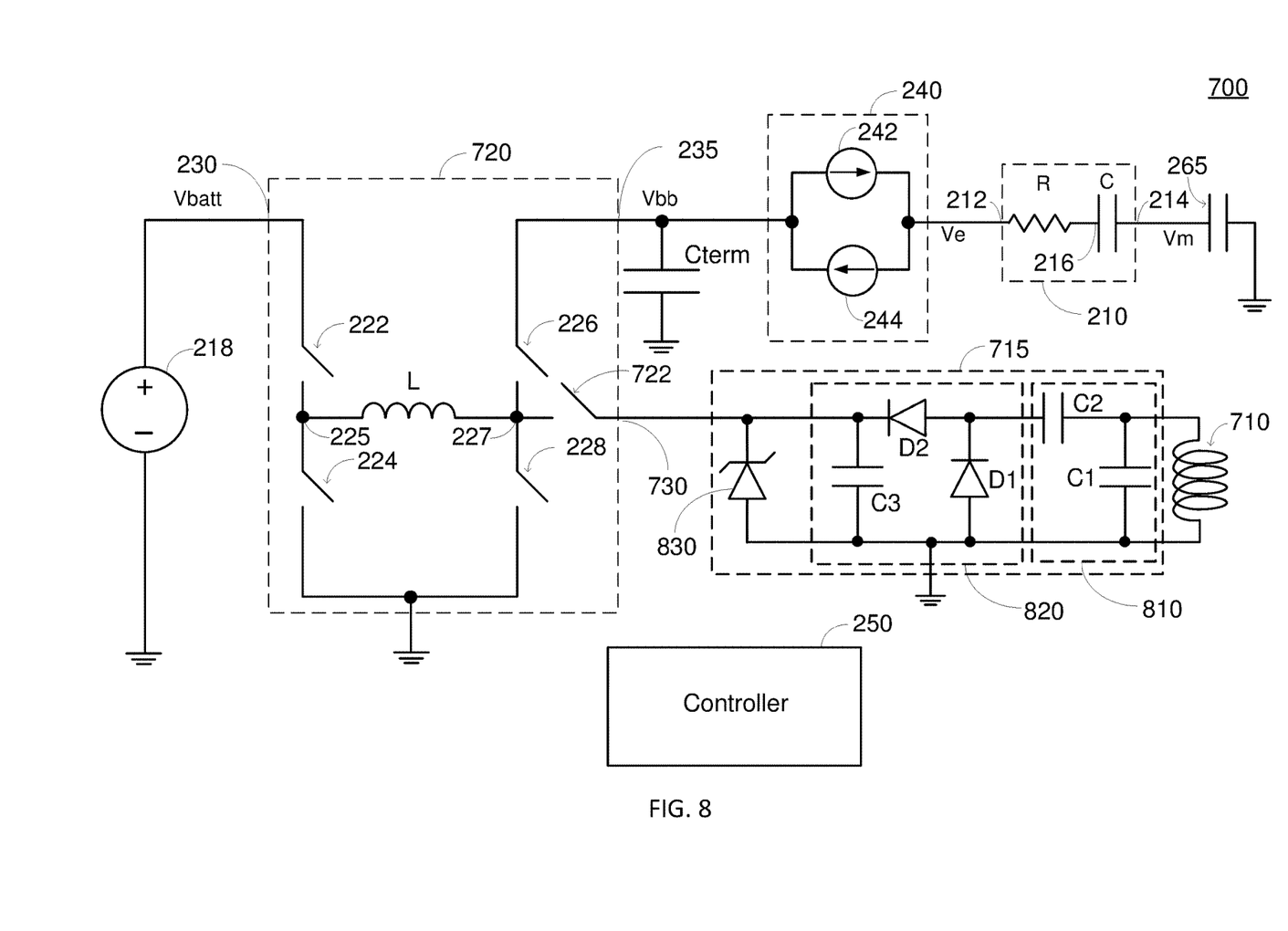
FIG. 8 shows an exemplary implementation of an interface circuit for the wireless charging coil according to certain aspects of the present disclosure.

FIG. 8 shows an exemplary implementation of the interface circuit 715 according to certain aspects of the present disclosure. In this example, the interface circuit 715 includes a tuning circuit 810, a rectifier 820, and a Zener diode 830.

The tuning circuit 810 include a first capacitor C1 and a second capacitor C2, in which the first capacitor C1 and the second capacitor C2 are coupled in series, and the first capacitor C1 is coupled in parallel with the wireless charging coil 710. The tuning circuit 810 may be configured to tune the resonance frequency of the wireless charging coil 710 to maximize the amount of energy harvested from the wireless signal.

The rectifier 820 includes a first diode D1, a second diode D2, and a third capacitor C3. The first diode D1 and the second diode D2 are coupled in series, and the first diode D1 is coupled in parallel with the tuning circuit 810. The diodes D1 and D2 are configured to rectify the AC signal from the coil 710, and the third capacitor C3 is configured to smooth the rectified signal to generate the DC voltage output to the switching regulator 220.

The Zener diode 830 is configured to provide voltage protection by limiting the maximum voltage level of the DC voltage. When the voltage level of the DC voltage reaches the breakdown voltage of the Zener diode 830, the Zener diode 830 provides a shunt to ground, thereby limiting the voltage level of the DC voltage to the breakdown voltage of the Zener diode 830.

Figure 9:
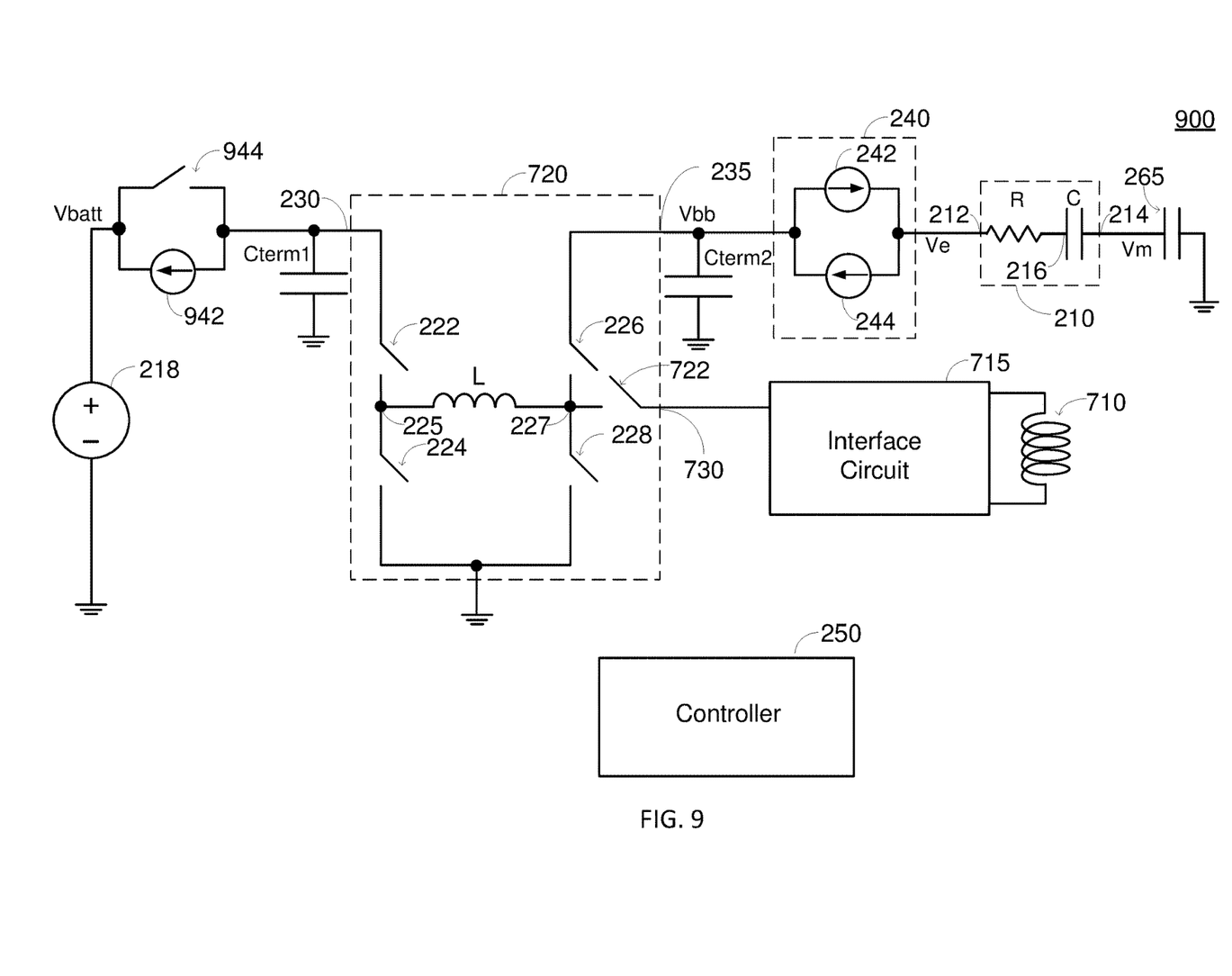
FIG. 9 shows an example of an electroceutical device including a current source for regulating current flow to and from a battery according to certain aspects of the present disclosure.

FIG. 9 shows an example in which the electroceutical device 900 further includes a current source 942 coupled between the battery 218 and the first terminal 230 of the switching regulator 220, a switch 944 coupled between the battery 218 and the first terminal 230 of the switching regulator 220, and a terminal capacitor Cterm1 coupled between the first terminal 230 of the switching regulator 220 and ground. In FIG. 9, the terminal capacitor coupled to the second terminal 235 of the switching regulator 220 is labeled "Cterm2" to distinguish this capacitor from the terminal capacitor Cterm1 coupled to the first terminal 230 of the switching regulator 220.

The current source 942 is configured to regulate current flow to the battery 218. The current source 942 may be implemented with a current mirror or another type of circuit. For ease of illustration, the connection between the controller 250 and the current source 942 is not shown in FIG. 9.

When the switching regulator 220 transfers energy from the electrode 210 or wireless charging coil 710 to the battery 218, the controller 250 activates the current source 942 and opens the switch 944. The current source 942 regulates the current flow to the battery 218. For example, the current source 942 may regulate the current flow to provide an approximately constant current to the battery 218.

When the switching regulator 220 transfers energy from the battery 218 to the electrode 210, the controller 250 closes switch 944 and deactivates the first current source 942. This couples the battery 218 to the first terminal 230, allowing current to flow from the battery 218 to the first terminal 230.

Figure 10:
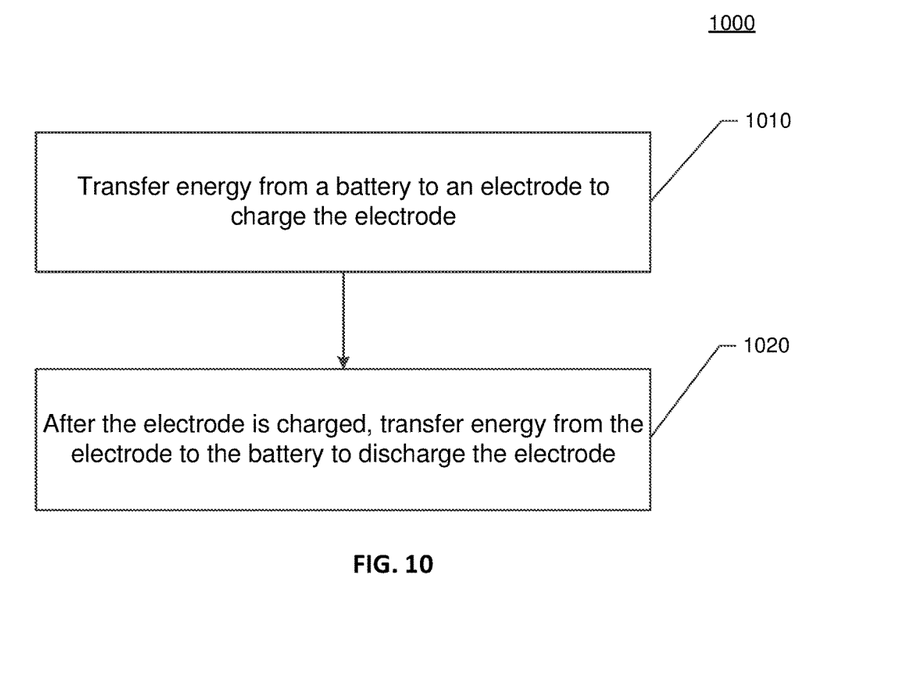
FIG. 10 is a flowchart showing a method for providing electrical stimulation according to certain aspects of the present disclosure.

FIG. 10 is a flowchart illustrating a method 1000 for providing electrical stimulation according to certain aspects of the present disclosure. The method 100 may be performed by any one of the electroceutical devices shown in FIGS. 2, 5, 7, 8 and 9.

In step 1010, energy is transferred from a battery to an electrode to charge the electrode. For example, energy may be transferred from the battery (e.g., battery 218) to the electrode (e.g., electrode 210) through an inductor (e.g., inductor L) over a first plurality of switching cycles. In each of the first plurality of switching cycles, the inductor may first be coupled to the battery to energize the inductor, and then coupled to the electrode to transfer energy in the inductor to the electrode.

In step 1020, after the electrode is charged, energy is transferred from the electrode to the battery to discharge the battery. For example, energy may be transferred from the electrode to the battery through the inductor over a second plurality of switching cycles. In each of the second plurality of switching cycles, the inductor may first be coupled to the electrode to energize the inductor, and then coupled to the battery to transfer energy in the inductor to the battery. The energy transferred from the electrode to the battery may include a portion of the energy transferred from the battery to the electrode during charging, thereby recycling the portion of the energy back to the battery. Note that some of the energy is lost through the resistor R.

It is to be appreciated that the present disclosure is not limited to the exemplary arrangement of switches shown in FIG. 2, and that other arrangements of switches may be used for the switching regulator. For example, to transfer energy from the first terminal 230 to the second terminal 235, other arrangements of switches may be used to couple the inductor L to the first terminal 230 to energize the inductor L using the battery 218, and then couple the inductor L to the second terminal 235 to transfer the energy in the inductor L to the second terminal 235. Similarly, other arrangements of switches may be used to couple the inductor L to the second terminal 235 or the third terminal 730 to energize the inductor L using the electrode 210 or charging coil 710, and then couple the inductor L to the first terminal 230 to transfer the energy in the inductor L to the first terminal 230. Thus, the present disclosure is not limited to a particular arrangement of switches for the switching regulator.

The controller 250 may be implemented with one or more processors and one or more memories storing instructions that, when executed by the one or more processors, cause the one or more processors to perform the operations discussed herein. The one or more processors may include general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any combination thereof. The one or more memories may be internal to the one or more processors and/or external to the one or more processors. The one or more memories may include any suitable computer-readable media, including RAM, ROM, Flash memory, EEPROM, etc.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples described herein but is to be accorded the widest scope consistent with the principles and novel features disclosed herein.

What is claimed is:

1. A device, comprising:
   a battery;
   an electrode, wherein the electrode is outside the battery;
   a switching regulator having a first terminal coupled to the battery, and a second terminal coupled to the electrode, wherein the switching regulator comprises
     an inductor,
     a first switch coupled between the first terminal of the switching regulator and a first terminal of the inductor,
     a second switch coupled between the first terminal of the inductor and a ground,
     a third switch coupled between the second terminal of the switching regulator and a second terminal of the inductor, and
     a fourth switch coupled between the second terminal of the inductor and the ground; and
   a controller configured to operate the switching regulator to charge and discharge the electrode, wherein, to charge the electrode, the controller operates the switching regulator to transfer energy from the battery to the electrode, and, to discharge the electrode, the controller operates the switching regulator to transfer energy from the electrode to the battery.

2. The device of claim 1, wherein the controller is configured to ramp up a voltage at the second terminal of the switching regulator during charging of the electrode.

3. The device of claim 2, wherein the controller is configured to ramp up the voltage at the second terminal of the switching regulator by adjusting a duty cycle of the switching regulator during charging of the electrode.

4. The device of claim 1, further comprising a bi-directional current source coupled between the second terminal of the switching regulator and the electrode, wherein the bi-directional current source is configured to regulate current flow between the second terminal of the switching regulator and the electrode.

5. The device of claim 4, wherein the controller is configured to adjust a voltage at the second terminal of the switching regulator during charging of the electrode to keep the voltage at the second terminal above a voltage of the electrode by a voltage margin.

6. The device of claim 5, wherein the voltage margin is equal to or less than twice a minimum overhead voltage for the current source to operate.

7. The device of claim 1, wherein, to charge the electrode, the controller is configured to operate the first, second, third and fourth switches over multiple switching cycle, each switching cycle including a first phase and a second phase, wherein, in the first phase of each cycle, the controller is configured to turn on the first and fourth switches and turn off the second and third switches, and, in the second phase of each cycle, the controller is configured to turn on the second and third switches and turn off the first and fourth switches.

8. The device of claim 1, wherein the switching regulator includes an inductor, and the switching regulator is configured to transfer energy between the battery and the electrode through the inductor.

9. The device of claim 1, wherein the energy transferred from the electrode to the battery includes a portion of the energy transferred from the battery to the electrode.

10. The device of claim 1, wherein the switching regulator includes an inductor, and the switching regulator is configured to transfer energy from the battery to the electrode through the inductor, and to transfer energy from the electrode to the battery through the inductor.

11. The device of claim 1, further comprising a capacitor, wherein a first terminal of the electrode is coupled to the switching regulator and a second terminal of the electrode is coupled to the capacitor.

12. The device of claim 11, wherein the controller is configured to pre-charge the capacitor to a voltage.

13. A device, comprising:
   a battery;
   an electrode, wherein the electrode is outside the battery;
   a switching regulator having a first terminal coupled to the battery, and a second terminal coupled to the electrode;
   a controller configured to operate the switching regulator to charge and discharge the electrode, wherein, to charge the electrode, the controller operates the switching regulator to transfer energy from the battery to the electrode, and, to discharge the electrode, the controller operates the switching regulator to transfer energy from the electrode to the battery; and a wireless charging coil coupled to a third terminal of the switching regulator, wherein the controller is configured to operate the switching regulator to transfer energy from the wireless charging coil to the battery to charge the battery.

14. The device of claim of 13, wherein the controller is configured to time multiplex the switching regulator between charging the battery using the wireless charging coil, and charging and discharging the electrode.

15. The device of claim 14, wherein the switching regulator includes an inductor, and the switching regulator is configured to transfer energy between the battery and the electrode through the inductor, and to transfer energy between the wireless charging coil and the battery through the inductor.

* * * * *